(12) United States Patent
Hsieh

(10) Patent No.: US 6,939,038 B2
(45) Date of Patent: Sep. 6, 2005

(54) ELECTRONIC EAR THERMOMETER WITH MULTIPLE MEASUREMENT AND MEMORY FUNCTION

(75) Inventor: Chin-Chih Hsieh, Yonghe (TW)

(73) Assignee: Innovatech Inc., Tortola (VG)

( * ) Notice: Subject to any disclaimer, the term of this patent is extended or adjusted under 35 U.S.C. 154(b) by 0 days.

(21) Appl. No.: 10/759,035

(22) Filed: Jan. 20, 2004

(65) Prior Publication Data

US 2005/0083993 A1 Apr. 21, 2005

(30) Foreign Application Priority Data

Oct. 21, 2003 (TW) ...................... 92218676 U

(51) Int. Cl.⁷ ............................ G01K 1/02; A61B 5/01
(52) U.S. Cl. ................. 374/186; 374/102; 374/128; 374/142; 702/131; 702/187; 600/474; 600/549; 128/920
(58) Field of Search ................... 374/101, 102, 374/108, 128, 142, 186; 702/131, 187; 600/549, 559, 474; 128/903, 904, 920

(56) References Cited

U.S. PATENT DOCUMENTS

| | | | | | |
|---|---|---|---|---|---|
| 3,940,742 A | * | 2/1976 | Hudspeth et al. | ........... | 600/549 |
| 4,121,574 A | * | 10/1978 | Lester | ........... | 702/131 |
| 4,321,933 A | * | 3/1982 | Baessler | ........... | 600/549 |
| 4,447,884 A | * | 5/1984 | Wada | ........... | 702/131 |
| 4,503,862 A | * | 3/1985 | Baessler | ........... | 600/549 |
| 4,790,324 A | * | 12/1988 | O'Hara et al. | ........... | 600/474 |
| 4,962,765 A | * | 10/1990 | Kung et al. | ........... | 600/549 |
| 5,181,521 A | * | 1/1993 | Lemelson | ........... | 600/549 |
| 6,110,124 A | * | 8/2000 | Cheng | ........... | 600/549 |
| 6,190,329 B1 | * | 2/2001 | Cheng | ........... | 600/549 |
| 6,332,867 B1 | * | 12/2001 | Chen et al. | ........... | 600/549 |
| 6,544,174 B2 | * | 4/2003 | West et al. | ........... | 128/903 |
| 6,790,178 B1 | * | 9/2004 | Mault et al. | ........... | 128/920 |
| 2001/0044588 A1 | * | 11/2001 | Mault | ........... | 600/549 |
| 2003/0130567 A1 | * | 7/2003 | Mault et al. | ........... | 600/300 |
| 2005/0059867 A1 | * | 3/2005 | Cheng | ........... | 600/549 |

* cited by examiner

*Primary Examiner*—Gail Verbitsky
*Assistant Examiner*—Stanley J. Pruchnic, Jr.

(57) ABSTRACT

A multiple measurement memory-type electronic thermometer includes an ear temperature measuring unit, a microprocessor, a keypad unit, a display unit, and a memory unit. The ear temperature measuring unit, the display unit, and the memory unit are controlled by the microprocessor. When the activation key of the keypad unit is pressed by the user, being controlled by the microprocessor, the ear temperature unit is activated to perform measurement. The measuring result of the ear temperature unit is sent back to the microprocessor, displayed by the display unit, and saved in the memory unit. The memory unit is partitioned into a plurality of independent memory sectors. Each sector includes a queue data structure, such that the ear temperature measured from each person and the measuring time can be stored in the corresponding memory sector. Therefore, measurement of multiple people can be performed, memorized and retrieved.

9 Claims, 3 Drawing Sheets

ELECTRONIC EAR THERMOMETER WITH MULTIPLE MEASUREMENT AND MEMORY FUNCTION

BACKGROUND OF THE INVENTION

The present invention relates to a multiple measurement electronic thermometer, and more particular, to an electronic ear thermometer operative to measure, memorize and display ear temperatures of multiple people.

The body temperature is a health indication of human body. The condition of human immunity system is typically monitored by temperature variation. Therefore, thermometer is an instrument required for every household. During the outbreak period of severe acute respiratory syndrome (SARS), various types of thermometers, particularly the convenient electronic ear thermometer, were out of supply. As the conventional ear thermometer can only display the current measurement, and the current measurement erased after a short period of time such as 5 seconds of display. Therefore, the temperature variation for one or more than one person cannot be traced unless additional recording medium is applied. Although some electronic ear thermometers have memory functions, they are limited to records of a single person. In other words, the measurement obtained from different persons cannot be distinguished by the electronic ear thermometers.

BRIEF SUMMARY OF THE INVENTION

The present invention provides an electronic ear thermometer having the function of multiple measurement and memory. By such electronic ear thermometer, the temperature measurement of every users obtained at different time can be recorded into individual memory sectors and retrieved therefrom. Therefore, the temperature variation of each user can be easily monitored.

The electronic ear thermometer provided by the present invention comprises a microprocessor serving as a control and a memory unit in electric communication therewith. The memory unit is partitioned into a plurality of memory sectors. Each memory sector is in the form of a queue data structure, such that the ear temperature measured from each individual can be saved into the corresponding memory sector. Therefore, the temperature measurement and history of each user can be retrieved as required.

These and other objectives of the present invention will become obvious to those of ordinary skill in the art after reading the following detailed description of preferred embodiments.

It is to be understood that both the foregoing general description and the following detailed description are exemplary, and are intended to provide further explanation of the invention as claimed.

BRIEF DESCRIPTION OF THE DRAWINGS

These, as well as other features of the present invention, will become apparent upon reference to the drawings wherein.

DETAILED DESCRIPTION OF THE INVENTION

Figure 1:
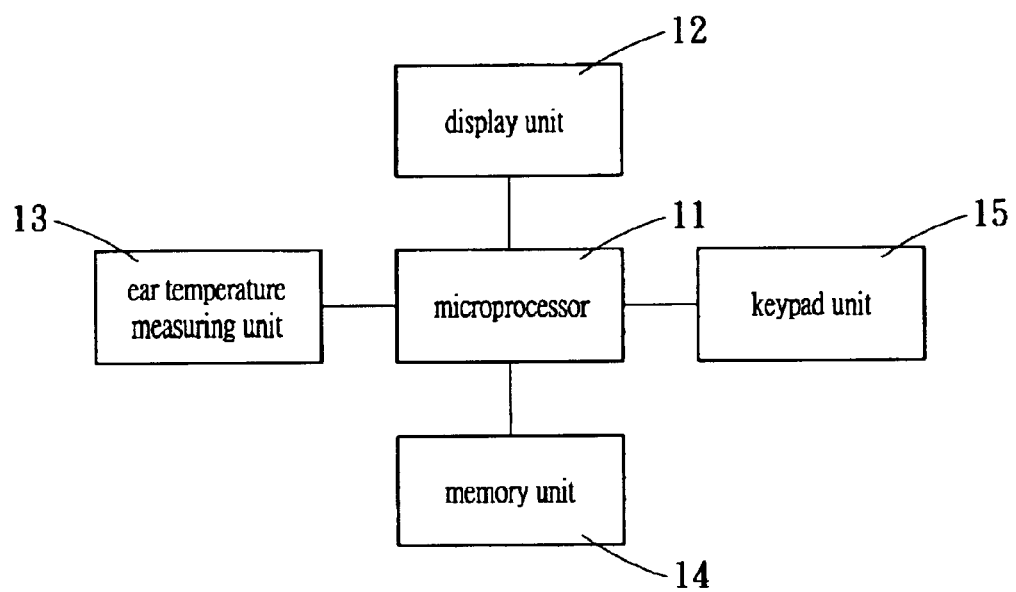
FIG. 1 shows a block diagram of the electronic ear thermometer provided by the present invention.

Reference will now be made in detail to the preferred embodiments of the present invention, examples of which are illustrated in the accompanying drawings. Wherever possible, the same reference numbers are used in the drawings and the description to refer to the same or like parts.

As shown in FIG. 1, the electronic ear thermometer provided by the present invention comprises a microprocessor 11, a display unit 12, an ear temperature measuring unit 13, a memory unit 14 and a keypad unit 15. The microprocessor 11 serves as a control center in electric communication with the display unit 12, the ear temperature measuring unit 13, the memory unit 14 and the keypad unit 15. When the user presses a key or a button of the keypad unit 15, an input signal is sent from the keypad unit 15 to the microprocessor 11. According to the input signal, the microprocessor 11 outputs a control signal to a specific unit to the display unit 12, the ear temperature measuring unit 13, and/or the memory unit 14 to perform required actions in accordance with the input signal. The display unit 12 includes a liquid crystal display (LCD) for displaying ear temperature, measuring time and the identification code for the user, for example. The memory unit 14 includes an electrically erasable and programmable read only memory (EEPROM) or a random accessible memory (RAM) operative to store data such as ear temperature and measuring time.

Figure 2:
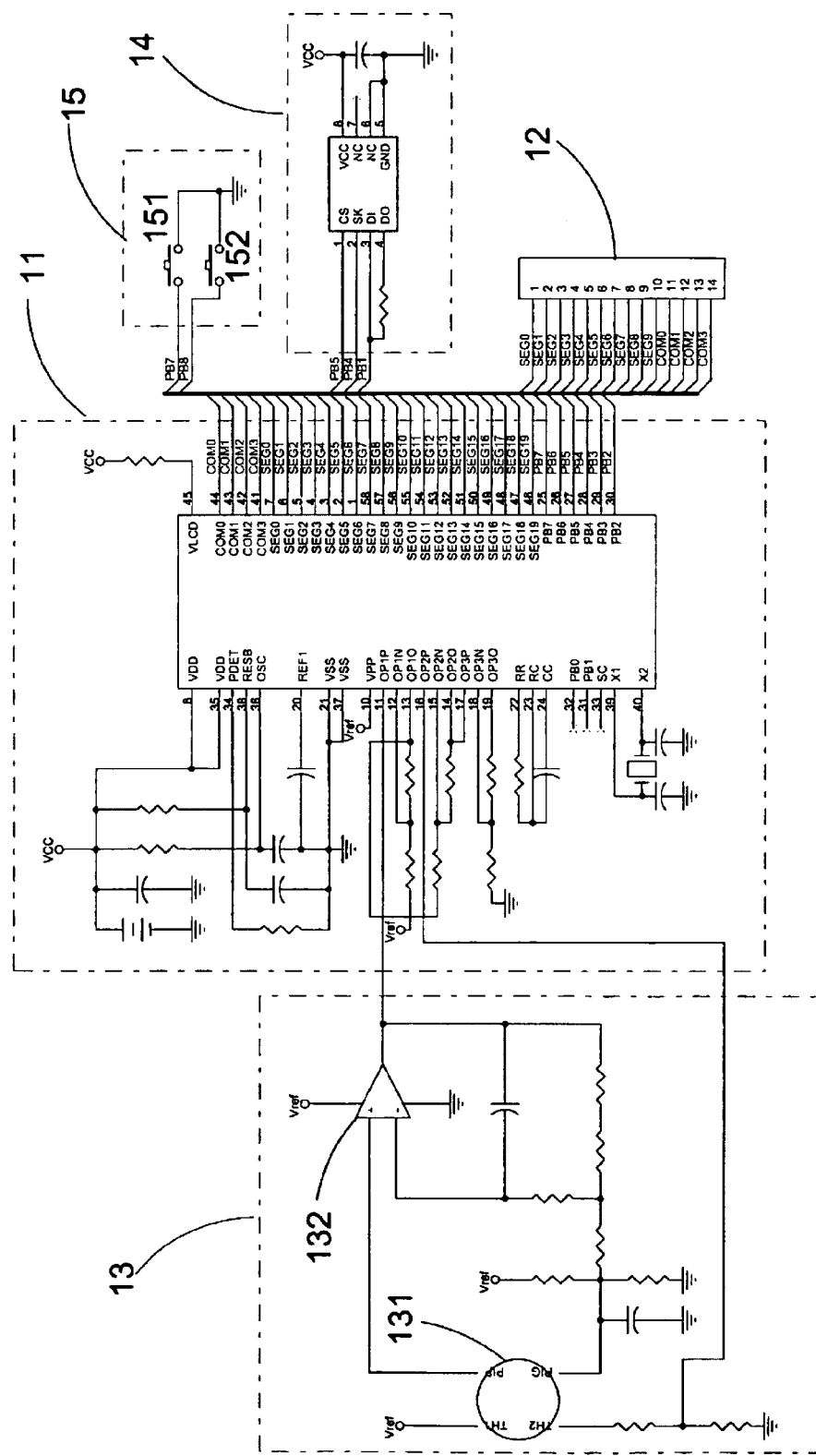
FIG. 2 shows a circuit diagram of the electronic ear thermometer.
Figure 3:
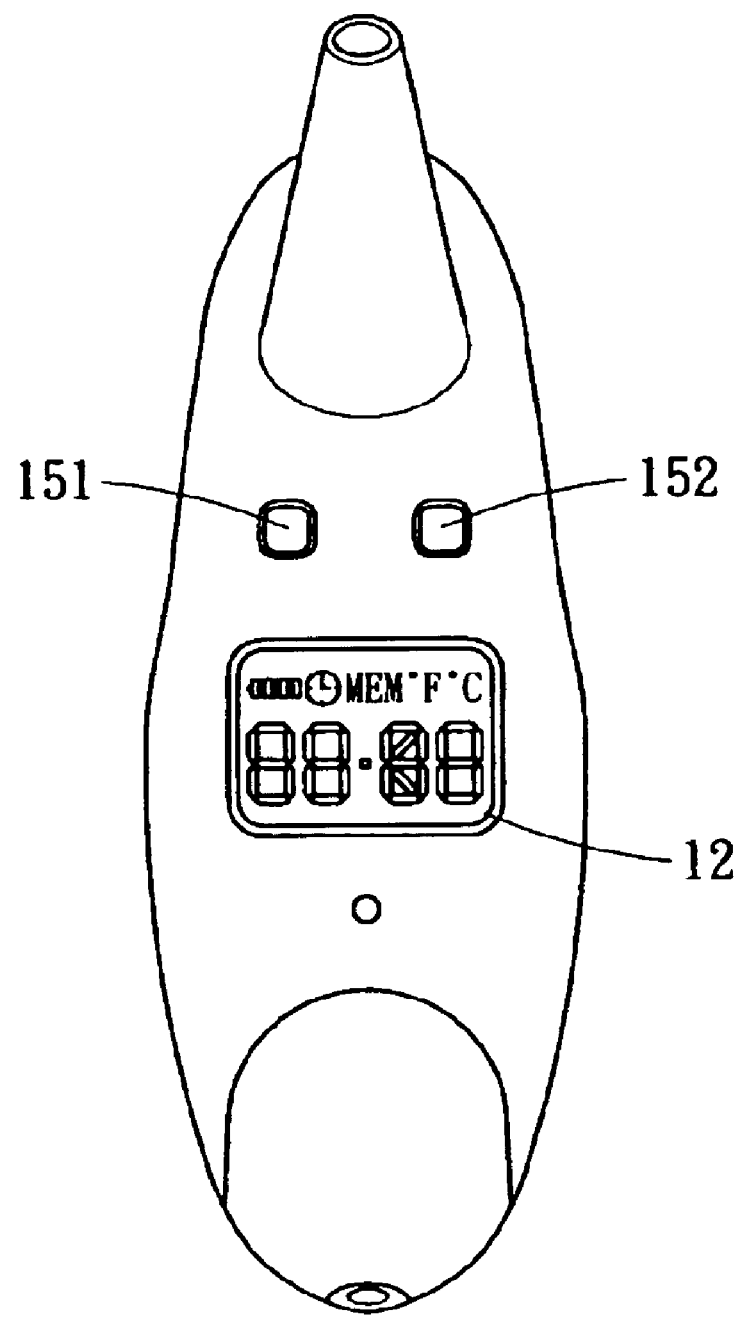
FIG. 3 shows a perspective view of the electronic ear thermometer.

FIG. 2 shows the circuit diagram of the electronic ear thermometer. As shown, the ear temperature measuring unit 13 includes a temperature sensor 131 operative to convert the measured temperature into an electric signal and an operation amplifier 132 to amplify the electric signal. The electric signal is then input to the microprocessor 11. The microprocessor 11 is operative to generate a control signal to the display unit 12 for displaying the temperature information carried by the electric signal input to the microprocessor 11. The microprocessor 11 is also operative to generate another control signal to the memory unit 14 for recording and saving the information carried by the electric signal. The memory unit 14 is partitioned into a plurality of memory sectors in the form of queues data structures. Therefore, the information is saved in a first in, first out manner. When the memory sector is full, the first-in data or information will be extruded to allow the current measurement to be saved therein. Therefore, the record saved in the memory sector is always the latest measurement of the user. For example, when each memory sector is operative to store only five sets of data, when the sixth measurement is performed, the first memory saved in the memory sector is erased from the memory sector while the sixth measurement is saved therein. The electronic ear thermometer also provides the functions of input the number of users by the number selection key 151 of the keypad unit 15. Further, identification code of each of the users such as user A and user B can also be defined by the keypad unit 15 as well. When the number of users and the identification code of the current user are input, the activation key 152 is pressed. Consequently, the temperature measurement is activated, and the measuring result is displayed by the display unit 12 and saved in the memory unit 14 under the control of the microprocessor 11. The measuring result includes not only the ear temperature, but also the duration of measurement. Therefore, the measuring history for each individual user can be properly maintained.

This disclosure provides exemplary embodiments of the present invention. The scope of this disclosure is not limited by these exemplary embodiments. Numerous variations, whether explicitly provided for by the specification or implied by the specification, such as variations in shape, structure, dimension, type of material or manufacturing process may be implemented by one of skill in the art in view of this disclosure.

What is claimed is:

1. A multiple measurement and memory electronic ear thermometer, comprising:

a keypad unit including an activation key and a selection key, wherein when the activation key is pressed, the keypad unit is operative to generate a first input signal and when the selection key is pressed, the keypad is operative to generate either a second input signal for selecting the number of users or a third input signal for selecting one of the users;

a microprocessor in electric communication with the keypad unit, the microprocessor being operative to generate a first control signal in response to the first input signal, a third control signal in response to the second input signal and a fourth control signal in response to the third input signal;

an ear temperature measuring unit, operative to measure ear temperature from a selected user in response to the first control signal generated by the microprocessor and convert the ear temperature into an electric signal sent to the microprocessor to generate a second control signal;

a display unit, operative to display the ear temperature in response to the second control signal; and a memory unit, being partitioned into an individual memory sector for each one of the users, wherein the memory sector is operative to save the ear temperature measurement in response to the second control signal and the fourth control signal or later to retrieve the stored ear temperature measurement in response to the fourth control signal.

2. The thermometer of claim 1, wherein each of the memory sectors is in the form of a queue data structure.

3. The thermometer of claim 1, wherein the display unit includes a liquid crystal display.

4. The thermometer of claim 1, wherein the memory unit includes an electrically erasable and programmable read only memory (EEPROM) or a random access memory (RAM).

5. The thermometer of claim 1, wherein the ear temperature measuring unit is also operative to count time for ear temperature measurement.

6. The thermometer of claim 1, wherein the keypad unit further includes a key for inputting an identification code for each user.

7. The thermometer of claim 1, wherein the ear temperature measuring unit is operative to measure ear temperature among different users in response to the actuating of the activation key or the selection key, wherein the ear temperature measurements can be stored, retrieved and displayed to/from the corresponding memory section of each user.

8. A multiple measurement and memory electronic ear thermometer, comprising: a keypad unit including an activation key and a selection key, wherein when the activation key is pressed, the keypad unit is operative to generate a first input signal and when the selection key is pressed, the keypad is operative to generate either a second input signal for selecting the number of users or a third input signal for selecting one of the users;

a microprocessor having a real time clock in electric communication with the keypad unit, the microprocessor being operative to generate a first control signal in response to the first input signal, a third control signal in response to the second input signal and a fourth control signal in response to the third input signal;

an ear temperature measuring unit, operative to measure ear temperature from a selected user in response to the first control signal generated by the microprocessor and convert the ear temperature into an electric signal sent to the microprocessor to generate a second control signal;

a display unit, operative to display the ear temperature and a measuring time from the real time clock in response to the second control signal; and a memory unit, being partitioned into individual memory sectors for each users, wherein the memory sector is operative to save the ear temperature measurement and the measuring time in response to the second control signal and the fourth control signal or later to retrieve and display the stored ear temperature measurement and the measuring time in response to the fourth control signal.

9. The ear thermometer claimed as claim 8, wherein the display unit can display a user identification with the ear temperature measurement and the measuring time.

* * * * *